United States Patent [19]

Fortunak et al.

[11] Patent Number: 5,468,859
[45] Date of Patent: Nov. 21, 1995

[54] PROCESS FOR ASYMMETRIC TOTAL SYNTHESIS OF CAMPTOTHECIN ANALOGUES

[75] Inventors: Joseph Fortunak, Exton, Pa.; John Kitteringham, Hertford, England; Nicholas Sisti, Jeffersonville; Jeffery Wood, Blue Bell, both of Pa.

[73] Assignee: SmithKline Beecham Corporation, Philadelphia, Pa.

[21] Appl. No.: 363,502

[22] Filed: Dec. 23, 1994

Related U.S. Application Data

[62] Division of Ser. No. 75,063, Jun. 10, 1993, Pat. No. 5,405,963.

[51] Int. Cl.$^6$ ............................................. C07D 491/22
[52] U.S. Cl. ............................................................ 546/48
[58] Field of Search ................................................ 546/48

[56] References Cited

U.S. PATENT DOCUMENTS 5,258,516   11/1993   Comins et al. .................. 546/116

*Primary Examiner*—Bernard Dentz
*Attorney, Agent, or Firm*—James M. Kanagy; Stuart R. Suter; Edward T. Lentz

[57] ABSTRACT

The present invention provides a process for the asymmetric synthesis of camptothecin analogs as well as novel chemical intermediates of Formula I, II, and III. In general, the present process comprises conversion of a cis dioxolanone, having the same desired absolute configuration as the desired camptothecin analog, to a compound of Formula I, II, or III, which compound is then converted to the desired camptothecin analog.

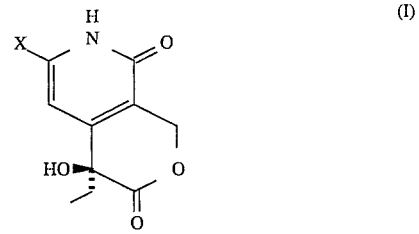

(I)

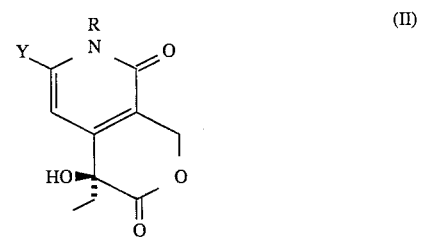

(II)

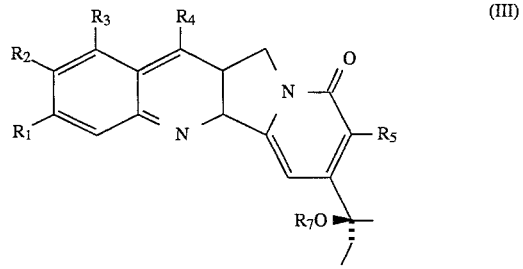

(III)

8 Claims, No Drawings

PROCESS FOR ASYMMETRIC TOTAL SYNTHESIS OF CAMPTOTHECIN ANALOGUES

This is a divisional of application Ser. No. 08/075,063, filed Jun. 10, 1993 now U.S. Pat. No. 5,405,963.

FIELD OF THE INVENTION

The present invention relates to chemical processes and novel chemical intermediates which are useful for preparing pharmaceutically important camptothecin analogues such as (S)- 10-[(dimethylamino)methyl]-4-ethyl-4,9-dihydroxy-1H-pyrano[3',4':6,7]indolizino[1,2 -b]quinoline-3,14(4H, 12H)dione monohydrochloride, commonly known as topotecan; or (S)- 4-ethyl-4,9-dihydroxy-1H-pyrano[3'4':6,7]indolizino[1,2-b]quinoline-3,14(4H,12H)dione, commonly known as 10-methoxycamptothecin, in high enantiomeric excess.

BACKGROUND OF THE INVENTION

Camptothecin analogues, such as topotecan, have been shown to be useful as both antineoplastic and antiviral therapeutic agents. A process for the total synthesis of racemic topotecan, a camptothecin analogue, is described in copending U.S. Ser. No. 07/941,496 now abandoned. A recent example of a different total synthesis was published by Comins, et al., *J. Am. Chem. Soc.*, 114, 10971, 1992. As is often the case, optimal therapeutic activity is provided by only one configuration of the molecule. It is therefore desirable to produce this material in a form which is highly enriched in only one absolute configuration of the chiral center.

A. I. Meyers et al., *J. Org. Chem.*, 38, 1973, 1974 describes the synthesis of racemic camptothecin analogues by the coupling of a carboxylic acid with a pyrrolo[3,4-b]quinoline. However, that process lacks the desirable ability to introduce chirality into the target camptothecin analogue.

SUMMARY OF THE INVENTION

An object of this invention is to provide novel chemical intermediates which are useful in the asymmetric synthesis of camptothecin analogues.

Another object of the present invention is to provide processes for preparing chemical intermediates useful in the asymmetric synthesis of camptothecin analogues.

In one aspect, this invention provides compounds according to Formulae (I), (II) or (III):

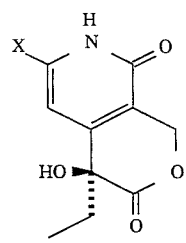

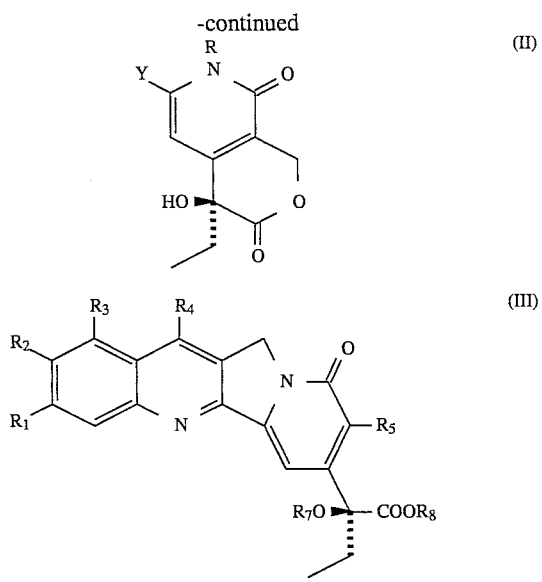

wherein:

X is selected from a group consisting essentially of a cyano group; a carboxylic acid; an N-aryl carboxylic acid derivative of Formula (A);

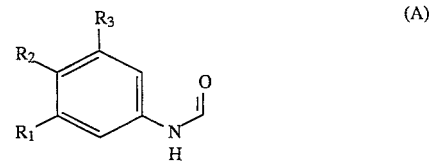

and a good leaving group, preferably a halide not including chloride, yet more preferably a bromide or iodide, most preferably bromide; or a sulfonate, more preferably a p-fluorobenzenesulfonate, trifluoromethanesulfonate or fluorosulphonate, most preferably trifluoromethanesulfonate;

Y is selected from a group consisting essentially of a cyano group; a carboxylic acid; an N-aryl carboxylic acid derivative of Formula (A);

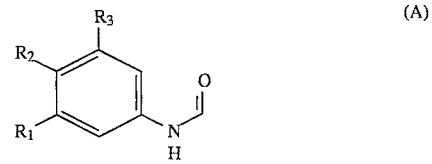

and a good leaving group, preferably a halide, more preferably a chloride, bromide or iodide, most preferably bromide; or a sulfonate, more preferably a p-fluorobenzenesulfonate, trifluoromethanesulfonate or fluorosulphonate, most preferably trifluoromethanesulfonate;

R is propargyl (i.e., —$CH_2C\equiv CH$) or substituted propargyl, as in Formula (B);

$R_1$ is hydrogen, or $R_1$ together with $R_2$ is —$OCH_2O$—;
$R_2$ is hydrogen; $O(C_1–C_6)$ alkyl, preferably methoxy;

OH; or $R_1$ together with $R_2$ is —OCH$_2$O—;

$R_3$ is hydrogen; OH; O(C$_1$–C$_6$) alkyl; NO$_2$; NH$_2$; or a protected nitrogen group which can be converted to NH$_2$, preferably trifluoroacetamido, acetamido, methoxycarbonylamino or carboxenzyloxyamino; preferably a p-fluorobenzenesulfonate, trifluoromethanesulfonate or fluorosulphonate, most preferably trifluoromethanesulfonate;

Y is selected from a group consisting essentially of a cyano group; a carboxylic acid; an N-aryl carboxylic acid derivative of Formula (A);

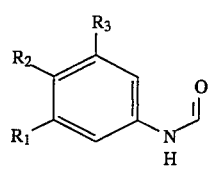

(A)

and a good leaving group, preferably a halide, more preferably a chloride, bromide or iodide, most preferably bromide; or a sulfonate, more preferably a p-fluorobenzenesulfonate, trifluoromethanesulfonate or fluorosulphonate, most preferably trifluoromethanesulfonate;

R is propargyl (i.e., —CH$_2$C≡CH) or substituted propargyl, as in Formula (B);

(B)

$R_1$ is hydrogen, or $R_1$ together with $R_2$ is —OCH$_2$O—;

$R_2$ is hydrogen; O(C$_1$–C$_6$) alkyl, preferably methoxy; OH; or $R_1$ together with $R_2$ is —OCH$_2$O—;

$R_3$ is hydrogen; OH; O(C$_1$–C$_6$) alkyl; NO$_2$; NH$_2$; or a protected nitrogen group which can be converted to NH$_2$, preferably trifluoroacetamido, acetamido, methoxycarbonylamino or carboxenzyloxyamino;

$R_4$ is hydrogen; SiMe$_3$; or alkyl, preferably methyl or ethyl;

$R_5$ is hydrogen or COOR$_6$;

$R_6$ is a carboxylic acid ester group, preferably methyl, ethyl, n-propyl, isopropyl, n-butyl, s-butyl, t-butyl, allyl or benzyl esters; and $R_7$ and $R_8$ are both hydrogen or $R_7$ together with $R_8$ is CH(t-butyl).

In another aspect, this invention provides novel methods for the asymmetric total synthesis of camptothecin analogues.

DETAILED DESCRIPTION OF THE INVENTION

Known methods for synthesizing camptothecin analogues primarily result in racemic products. However, the antiviral or antineoplastic activity of camptothecin analogues has been observed to vary with enantiomeric purity. That is, one enantiomer of a given analogue exhibits superior antiviral or antineoplastic activity when compared with that of the other enantiomer. For example the unnatural enantiomer of camptothecin (R) exhibits cytotoxicity without having the specific anticancer activity associated with the naturally-occurring enantiomer (S). The compounds of the present invention, represented by the Formulae (I), (II), and (III):

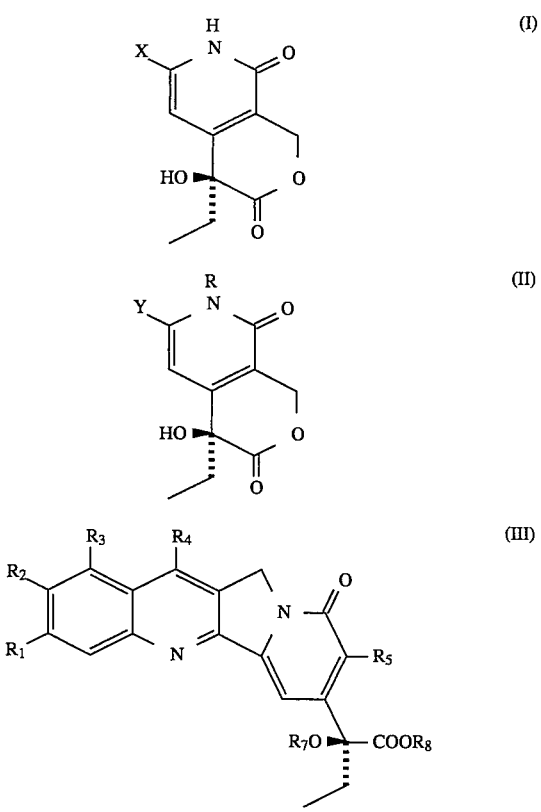

wherein:

X is selected from a group consisting essentially of a cyano group; a carboxylic acid; an N-aryl carboxylic acid derivative of Formula (A);

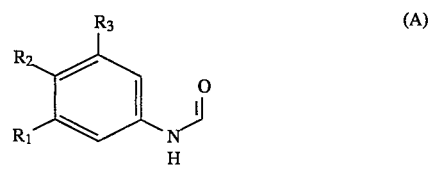

(A)

and a good leaving group, preferably a halide not including chloride, more preferably a bromide or iodide, most preferably bromide; or a sulfonate, more preferably a p-fluorobenzenesulfonate, trifluoromethanesulfonate or fluorosulphonate, most preferably trifluoromethanesulfonate;

Y is selected from a group consisting essentially of a cyano group; a carboxylic acid; an N-aryl carboxylic acid derivative of Formula (A);

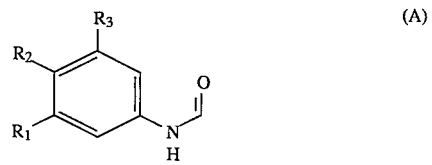

(A)

and a good leaving group, preferably a halide, more preferably a chloride, bromide or iodide, most preferably bromide; or a sulfonate, more preferably a p-fluorobenzenesulfonate, trifluoromethanesulfonate or fluorosulphonate, most preferably trifluoromethanesulfonate;

R is propargyl (i.e., —CH$_2$C≡CH) or substituted propargyl, as in Formula (B);

(B)

R$_1$ is hydrogen, or R$_1$ together with R$_2$ is —OCH$_2$O—;

R$_2$ is hydrogen; O(C$_1$–C$_6$) alkyl, preferably methoxy; OH; or R$_1$ together with R$_2$ is —OCH$_2$O;

R$_3$ is hydrogen; OH; O(C$_1$–C$_6$) alkyl; NO$_2$; NH$_2$; or a protected nitrogen group which can be convened to NH$_2$, preferably, trifluoroacetamido, acetamido, methoxycarbonylamino or carboxenzyloxyamino;

R$_4$ is hydrogen; SiMe$_3$; or alkyl, preferably, methyl or ethyl;

R$_5$ is hydrogen or COOR$_6$;

R$_6$ is a carboxylic acid ester group, preferably methyl, ethyl, n-propyl, isopropyl, n-butyl, s-butyl, t-butyl, allyl or benzyl esters; and R$_7$ and R$_8$ are both hydrogen or R$_7$ together with R$_8$ is CH(t-butyl), are useful as chemical intermediates in the production of camptothecin analogues by the asymmetric syntheses of the present invention.

The following terms have the meanings defined below here and throughout this application.

The term "good leaving group" means any chemical moiety which one of ordinary skill in the art would understand to be sufficiently electrophilic so as to readily undergo nucleophilic substitution in the presence of a nucleophile, for example chloride, bromide, iodide, p-fluorobenzenesulfonate, trifluoromethylsulfonate or fluorosulphonate.

The term "protected nitrogen group which can be convened to NH$_2$," includes any chemical moiety which one of ordinary skill in the art would understand to be the protected equivalent of —NH$_2$ and capable of readily being deprotected by known methods to —NH$_2$, preferably trifluoroacetamido, acetamido, methoxycarbonylamino or carboxenzyloxyamino.

The term "alkyl" includes common C$_1$–C$_6$ saturated hydrocarbon chains such as methyl, ethyl, n-propyl, isopropyl, n-butyl, s-butyl and t-butyl.

The term "camptothecin" includes camptothecin and any derivative thereof the structure of which is based on the 1H-pyrano[3',4':6,7]indolizino-[1,2-b]quinolin-3,14(4H,12H)-dione ring system.

The terms "1H-pyrano[3'4':6,7]quinoline", "indolizino[1,2-b]quinolin-9(11H)-one" and "1H-pyrano[3',4':6,7]indolizino-[1,2-b]quinolin-3,14(4H,12H)-dione" refer generally to compounds based on these ring systems.

The term "camptothecin analogue" includes camptothecins as defined above and also includes derivatives of camptothecin wherein the E ring has been replaced with another functionality.

The term "carboxylic acid" refers to —COOH.

The term "cyano group" refers to C≡N.

The term "carboxylic acid ester groups" refers to methyl, ethyl, n-propyl, isopropyl, n-butyl, s-butyl, t-butyl, allyl and benzyl esters.

The term "strong alkylating agent" includes agents capable of producing either an O-alkylimidate or imidate ester, imidoyl halide, or imide derivative in the process of the present invention.

The following section discloses how to make the intermediate compounds of the present invention and also discloses the processes of the present invention. The first process of the present invention is illustrated in Schemes 1–4. In general this process comprises:

a) forming a chiral cis dioxolanone having a carboxylic acid function, the cis dioxolanone having the absolute configuration desired in the camptothecin analogue;

b) forming a pyrrolo[3,4-b]quinoline having a free amine function;

c) reacting the cis dioxolanone with the pyrrolo[3,4-b]quinoline to form a compound of Formula (III)

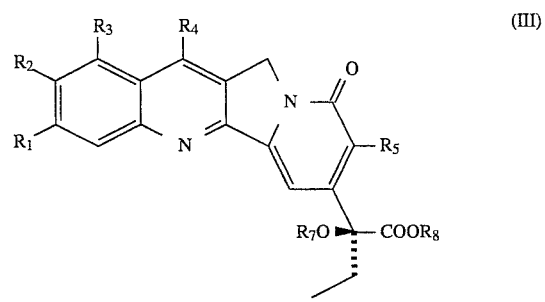
(III)

wherein:

R$_1$ is hydrogen or R$_1$ together with R$_2$ is —OCH$_2$O—, preferably hydrogen;

R$_2$ is hydrogen; O(C$_1$—C$_6$)alkyl, preferably methoxy; OH; or R$_1$ together with R$_2$ is —OCH$_2$O—;

R$_3$ is hydrogen; OH; O(C$_1$–C$_6$)alkyl; NO$_2$; NH$_2$; or a protected nitrogen which can be convened to NH$_2$, preferably hydrogen;

R$_4$ is hydrogen; SiMe$_3$; or alkyl, preferably hydrogen or alkyl, the most preferred alkyl being ethyl;

R$_5$ is hydrogen or COOR$_6$;

R$_6$ is a carboxylic acid ester group, preferably methyl, ethyl, n-propyl, isopropyl, n-butyl, s-butyl, t-butyl, allyl or benzyl esters, most preferably methyl ester; and R$_7$ and R$_8$ together form CH(t-butyl); and d) convening the compound of Formula (III) into a camptothecin analogue.

Schemes 6 and 7 illustrate the second process of the present invention. In general this process comprises:

a) forming a chiral cis dioxolanone having the absolute configuration desired in the camptothecin analogue;

b) convening the cis dioxolanone to a compound of Formula (I)

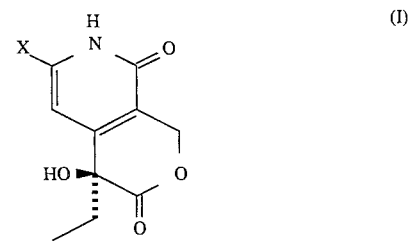
(I)

wherein X is selected from a group consisting of a good leaving group, preferably a halide not including chloride, more preferably a bromide or iodide; or a sulfonate, more preferably, p-fluorobenzenesulfonate, trifluoromethanesulfonate or fluorosulphonate; a cyano group; a carboxylic acid; and an N-aryl carboxylic amide derivative of Formula (A);

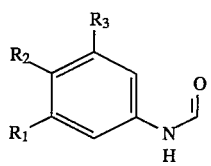

c) converting said compound of Formula (I) into a compound of Formula (II)

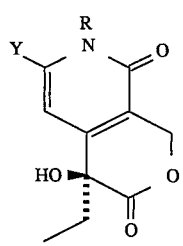

wherein:

R is propargyl or substituted propargyl of Formula (B);

and

Y is selected from a group consisting of a good leaving group, a cyano group, a carboxylic acid, and an N-aryl carboxylic amide derivative of Formula (A); and

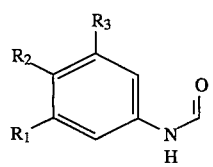

d) converting the compound of Formula (II) into a camptothecin analogue.

Both processes rely on the use of a chiral 1,3 dioxolan-4-one to introduce the desired absolute configuration into the desired camptothecin analogue product.

Chiral 1,3-dioxalan-4-one is prepared from commercially available R-2-aminobutyric acid. Diazotisation of the amino acid with sodium nitrite and sulfuric acid is accompanied by the displacement of the diazo group with complete retention of configuration to give R-2-hydroxybutyric acid. Similar reactions have been described by K. Mori, et al. in *Tetrahedron*, 35, 1601, 1979. The chiral hydroxyl-bearing carbon eventually becomes the chiral center (C-20) of the camptothecin molecule. This hydroxyacid is converted to the corresponding acetal, (1) in Scheme 1, with a very high stereoselectivity (greater than 20:1) for formation of the cis dioxolanone. This specific reaction was disclosed by K. Krohn, et al. in *Annalen Der Chemie.*, 949, 1988, although we have modified these authors' reaction conditions to achieve an improved stereoselectivity over their reported results (improved from about 10–14:1). Recrystallization of the dioxolanone at low temperature (−70° C.) from hexane:ether gives the essentially pure (>99%) cis isomer. This step allows control of the absolute stereochemistry of the chiral center of camptothecin, since all subsequent chemical operations are carried out with retention of the configuration at this carbon. This approach to control of absolute stereochemistry is useful in the preparation of camptothecin and its analogues in essentially complete enantiomeric purity by either of the two processes of the present invention.

SCHEME 1

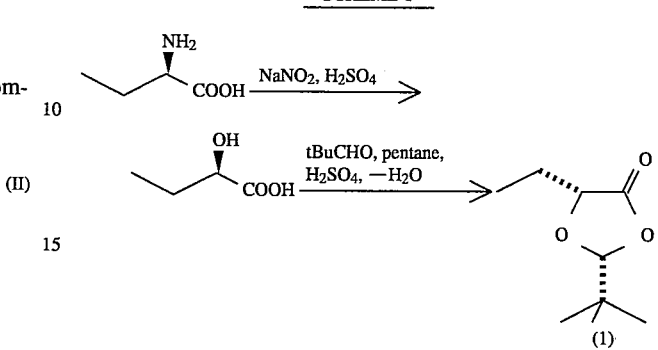

Step a) of the first process is described as follows. Scheme 1 illustrates a process for making the dioxolanone starting material. As shown in Scheme 2 Knoevenagel condensation of the commercially available mono-methyl acetal of glyoxaldehyde with methylbenzylmalonate gives methylene malonate (2). Subsequent Michael addition of an enolate, preferably the lithium enolate, of (1) gives compound (3), in which the stereochemistry of the dioxolanone is as shown. Refer to, D. Seebach, et al. in "Modern Synthetic Methods, 1986" R. Scheffold ed. pages 125–259 for a discussion of the control of the stereoselectivity observed in the product. This reaction establishes the absolute configuration of the chiral center, eventually leading to the desired (S)-camptothecins, since all subsequent operations are carried out without affecting the stereochemical integrity of this center. Hydrogenolysis of the benzyl ester produces the corresponding acid (4).

SCHEME 2

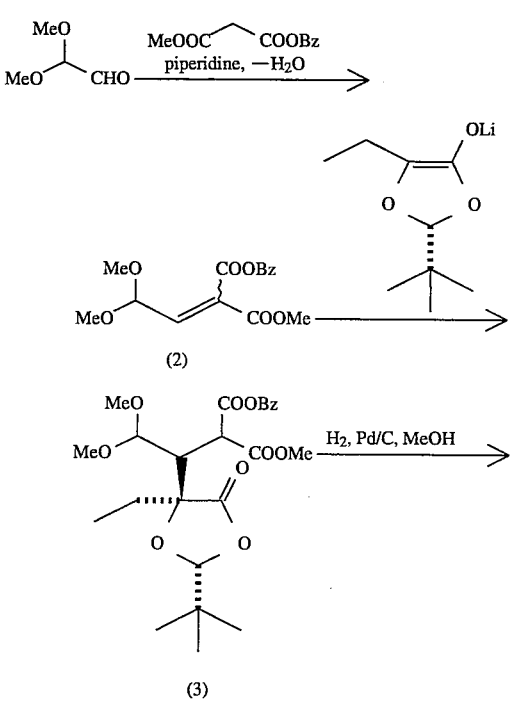

-continued
SCHEME 2

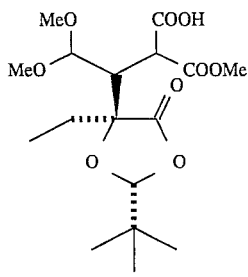

(4)

In step b) of the first process of the present invention, the substituted pyrrolo[3,4-b] quinoline (6) is prepared as shown in Scheme 3. Para-anisidine is acylated on nitrogen using bromoacetyl bromide (or optionally, chloroacetyl chloride). The remaining, alkyl bromide (or chloride) group is subsequently displaced in an $S_N2$ reaction using propargylamine, and the secondary amine nitrogen is protected by forming the corresponding carbamate derivative with methyl chloroformate to yield (5). Compound (5) is reacted in a polar solvent, preferably methylene chloride, 1,2-dichloroethane, 1,2-dimethoxyethane, tetrahydrofuran, N,N-dimethylformamide, acetonitrile, acetone or N-methylpyrrolidinone, most preferably acetonitrile; at a starting temperature of about −30° C., followed by warming to a temperature of about 20°–85° C., preferably at 40°–85° C., most preferably at a temperature of 40°–50° C.; in the presence of a strong alkylating agent or such agent as is capable of producing either an O-alkylimidate or imidate ester, imidoyl halide, or such imide derivative defined herein and throughout this application as "imidate/imidoyl halide derivative"; preferably trifluoromethanesulfonic anhydride, dimethylsulfate, alkyloxonium tetrafluoroborates, aluminum chloride, O-benzyltrichloroacetimidate, triphenylphosphine/carbon tetrachloride, or triphenylphosphine/carbon tetrabromide, most preferably trimethyloxonium tetrafluoroborate. The resulting imidate/imidoyl halide derivative then undergoes [4+2] cycloaddition and subsequent elimination of methanol (in the case in which an O-methyl imidate ester is initially formed) or hydrogen halide (in the case in which an imidoyl halide is initially formed) or a sulfonic acid (in the case in which an imidate ester is initially formed) to yield a substituted pyrrolo[3,4-b]quinoline (6). This transformation has also been described in U.S. Ser. No. 07/941,496.

In step c) of the first process of the present invention, the carboxylic acid functionality of the cis dioxolanone is reacted with the pyrrolo[3,4-b]quinoline at the amine function to form an amide having a dimethyl acetal function. This dimethyl acetal function of the amide is then hydrolyzed to form an aldehyde. Intramolecular aldol condensation of this aldehyde, followed by aromatization, yields a compound of Formula (III).

SCHEME 3

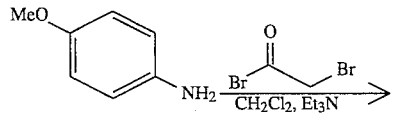

-continued
SCHEME 3

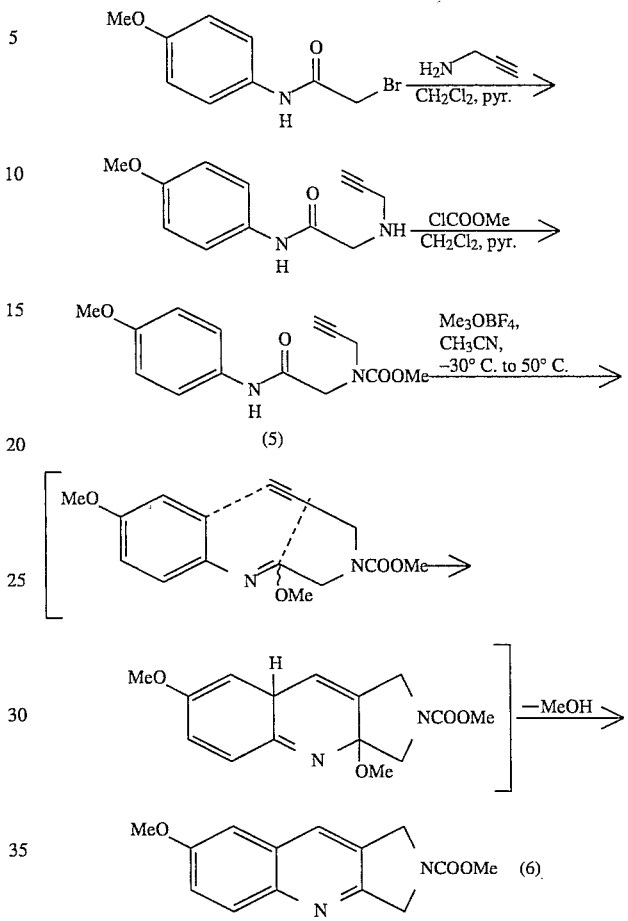

In particular, amine (7) is prepared from (6) by hydrolysis of the carbamate function with acetic acid saturated with hydrobromic acid as shown in Scheme 4. This intermediate is coupled with the carboxylic acid (4) prepared as in Scheme 2 by utilizing 1-(3-dimethylaminopropyl)-3 -ethyl-carbodiimide (abbreviated WSCD for "water-soluble carbodiimide" in the Scheme) and hydroxybenzotriazole (abbreviated HOBT) to give the resulting amide (8). The dimethyl acetal function is hydrolyzed with boron trifluoride etherate to give the resulting aldehyde (9). Aldol condensation using trifluoroacetic acid to promote the elimination of water, with subsequent aromatisation, using 2,3-dichloro-5,6-dicyano-1,4-benzoquinone (DDQ) as an oxidizing agent, gives the aromatic D-ring skeleton of the camptothecins shown, with (10a) as the major product. This product is an intermediate compound of the present invention of Formula (III).

In step d) of the first process of the present invention, this intermediate of Formula (III), wherein $R_5$ is methyl ester, undergoes reduction at the methyl ester to an alcohol function, followed by intramolecular lactone formation to form a camptothecin analogue. For example, subsequent reduction of the methyl ester of (10a) to the corresponding alcohol and closure of the E ring lactone by basic hydrolysis of the dioxolanone ring and subsequent acidification gives an asymmetric total synthesis of (S)-10-methoxycamptothecin (11).

SCHEME 4
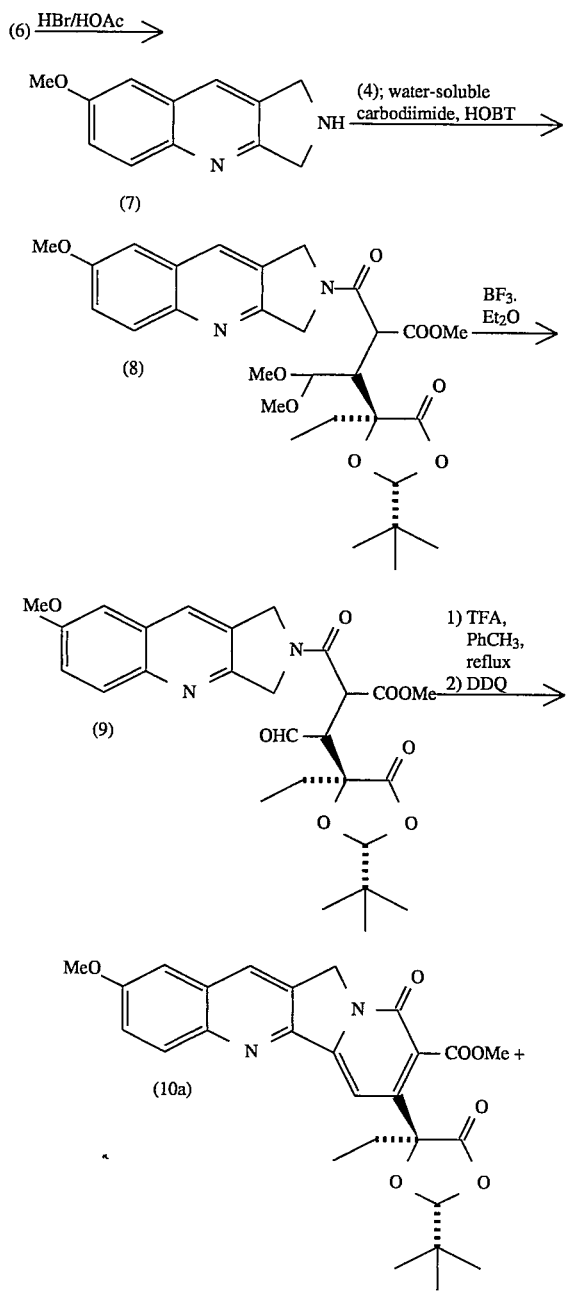
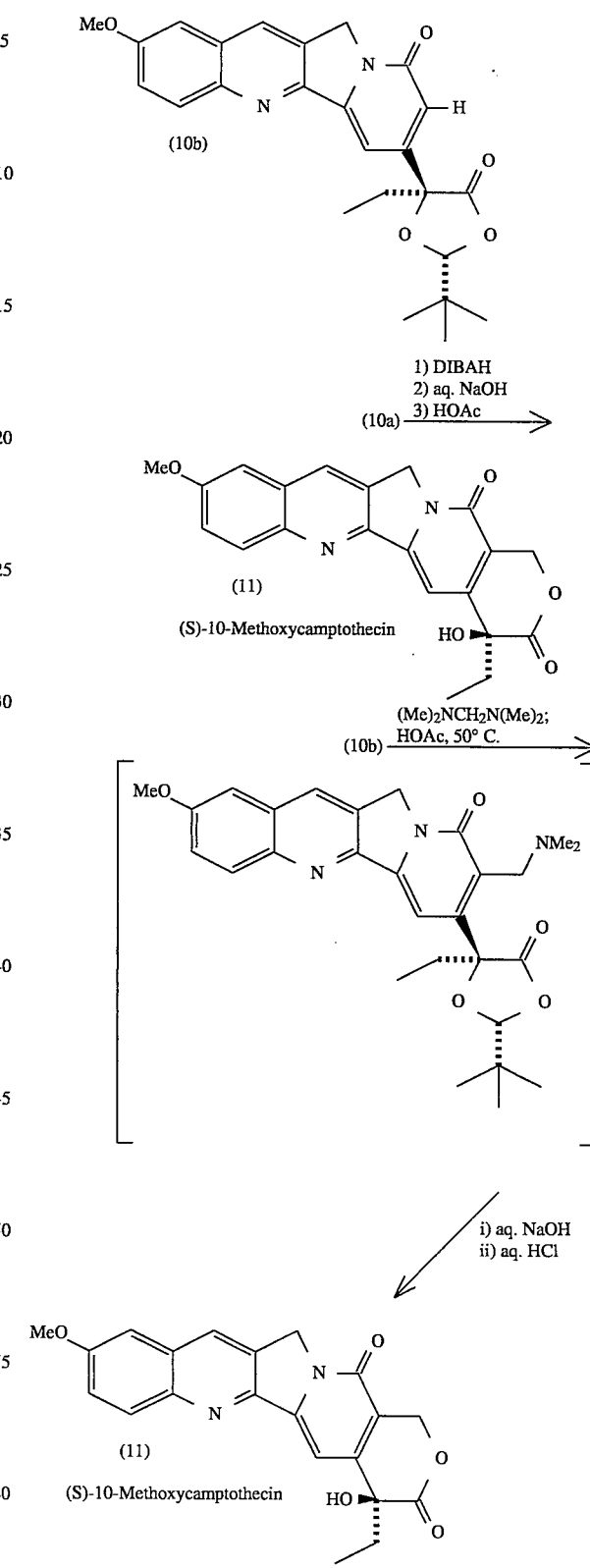

Alternatively, in step c) of the first process, reacting a cis dioxolanone with a pyrrolo[3,4-b]quinoline also results in a product of Formula (III), wherein $R_5$ is hydrogen. In general, this compound is convened to a camptothecin analogue by a process comprising:
1) forming a Mannich reagent known as 1,1,3,3-tetramethyl-diaminomethane;
2) reacting the Mannich reagent with the compound of Formula (III), wherein $R_5$ is hydrogen, in a reaction mixture to form a N,N-dimethylaminomethylated intermediate;
3) treating the reaction mixture with an aqueous base; and
4) acidifying the reaction mixture to precipitate a camptothecin analogue.

This process is exemplified in Scheme 4 in which compound (10b) is isolated as a byproduct of the reaction/ isolation sequence used to prepare (10a). This product arises from (10a) by decarbomethoxylation, apparently during chromatographic isolation. Compound (10b) is also easily converted to (S)-10-methoxycamptothecin using a novel process which yields a significant improvement upon existing knowledge. The hydroxymethylation of compound (A) shown in Scheme 5 was reported by Danishefsky et al., *J. Am. Chem. Soc.*, 94, 5576, 1972 to proceed upon treatment of the substrate with paraformaldehyde in dioxane containing concentrated sulfuric acid (100° C., 16 hours) to yield the precursor of racemic camptothecin which lacks only the required hydroxyl group at C-20. However, this is a difficult reaction to carry out, typically giving the desired product in only a low (approximately 25%) yield. The process of the present invention provides a greatly improved conversion of compound (10b) to (S)-10-methoxycamptothecin. By utilizing a reactive, pre-formed Mannich reagent (1,1,3,3-tetramethyl-diaminomethane), compound (10b) can be very readily N,N-dimethylaminomethylated (rather than hydroxymethylated). This intermediate is not isolated (refer to Scheme 4) but rather worked up by sequential treatment with aqueous base to displace dimethylamine and concurrently hydrolyze the acetal of the dioxolanone ring. This is followed by acidification to close the lactone ring and precipitate the desired product, (S)-10-methoxycamptothecin in very good (65%) overall yield.

SCHEME 5

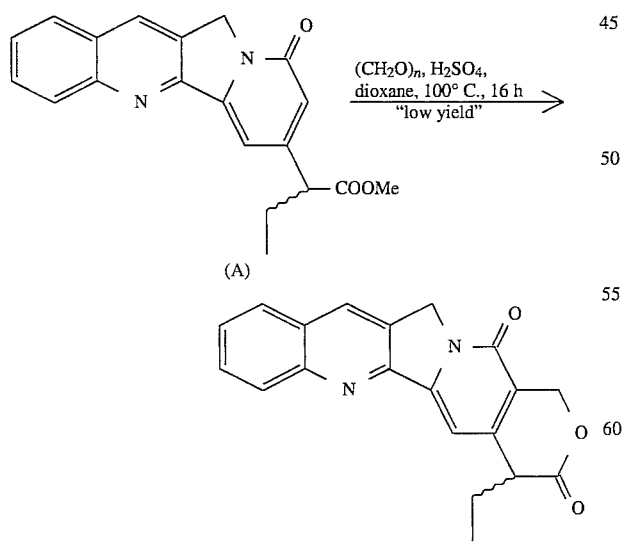

A second process of the present invention for the synthesis of camptothecins possessing the natural enantiomeric configuration can also be executed utilizing chiral dioxolanone (1). This process, which is outlined in Schemes 6 and 7, is substantially different from the above-described process of the present invention. The chiral cis dioxolanone having a diester function described in step a) of the second process can be formed by Michael addition of an enolate of dioxolanone to diethyl glutaconate. Specifically, the dioxolanone enolate derived from (1) is added in a Michael fashion (1,4-addition) to diethyl glutaconate to give diester (12).

In step b) of the second process, the cis dioxolanone is converted to a compound of Formula (I), wherein X is preferably a good leaving group, more preferably chloride, bromide or iodide, most preferably bromide, by hydrolysis of the diester function of the dioxolanone, followed by ring closure to form a corresponding glutarimide and treatment of the glutarimide with an excess of a thionyl halide, preferably thionyl bromide, in dimethylformamide, followed by workup in aqueous base. The diester is then in this fashion hydrolyzed and ring-closed to give the corresponding glutarimide (13) by treatment with ammonia in acetic acid. The glutarimide is then treated with excess thionyl chloride or thionyl bromide in the presence of N,N-dimethylformamide. Workup with aqueous base, followed by neutralization results in the formation of bicyclic intermediate (14a). While not wishing to be bound to any particular mechanism of action, it is believed that this step proceeds by the following mechanism. Thionyl halide converts N,N-dimethylformamide into the corresponding N,N-dimethyliminium halide (Vilsmeier reagent) which serves to formylate the glutarimide ring at a position adjacent to one of the carbonyl groups. The other carbonyl group of the glutarimide is converted in the same process to the corresponding vinyl halide by the action of excess thionyl halide. Workup with a basic aqueous solution then generates the isolated product. During the course of workup a prototropic shift occurs, causing rearrangement of the exocyclic aldehyde function to give the corresponding hydroxymethyl pyridone. The hydroxymethyl group closes onto the carbonyl group of the chiral dioxolanone, ultimately resulting in loss of pivalaldehyde and formation of what will become the E ring lactone of camptothecin with an absolute configuration identical to that possessed by the natural product.

Alternatively, Compound (13), may be treated with a powerful sulfonylating agent such as trifluoromethanesulfonic anhydride (triflic anhydride) in the presence of N,N-dimethylformamide, resulting in a product (14b) which is a vinyl sulfonate analogue of vinyl halides (14a).

SCHEME 6

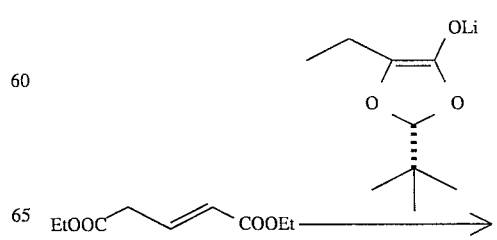

-continued
SCHEME 6

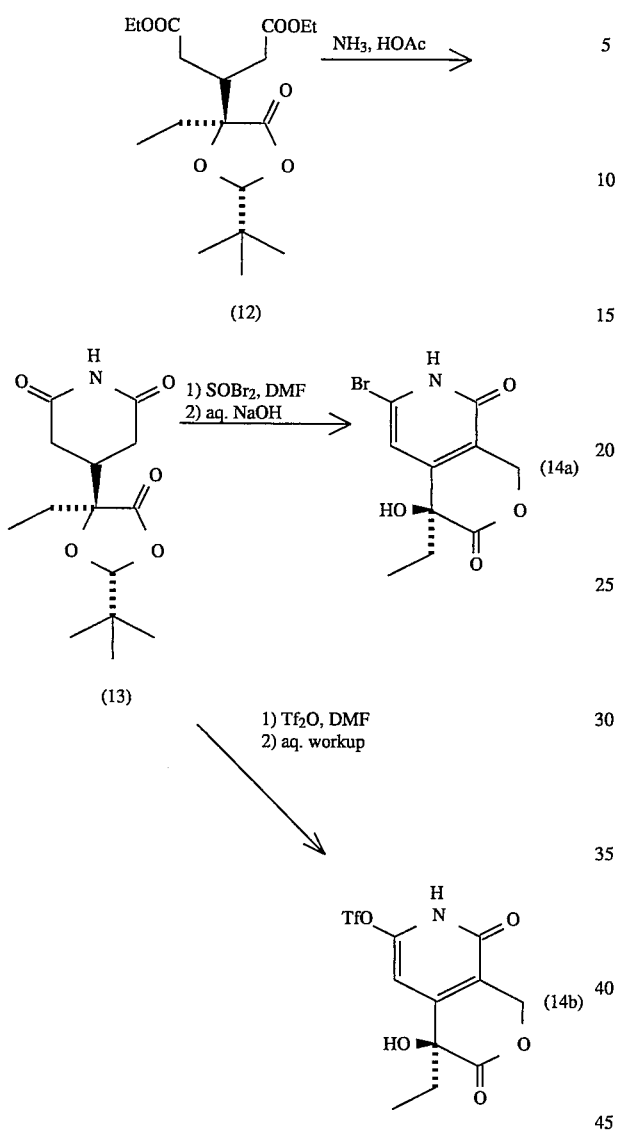

SCHEME 7

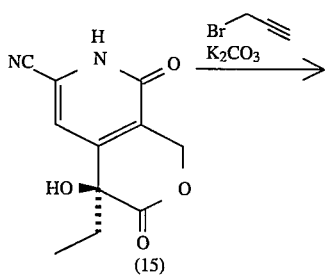

-continued
SCHEME 7

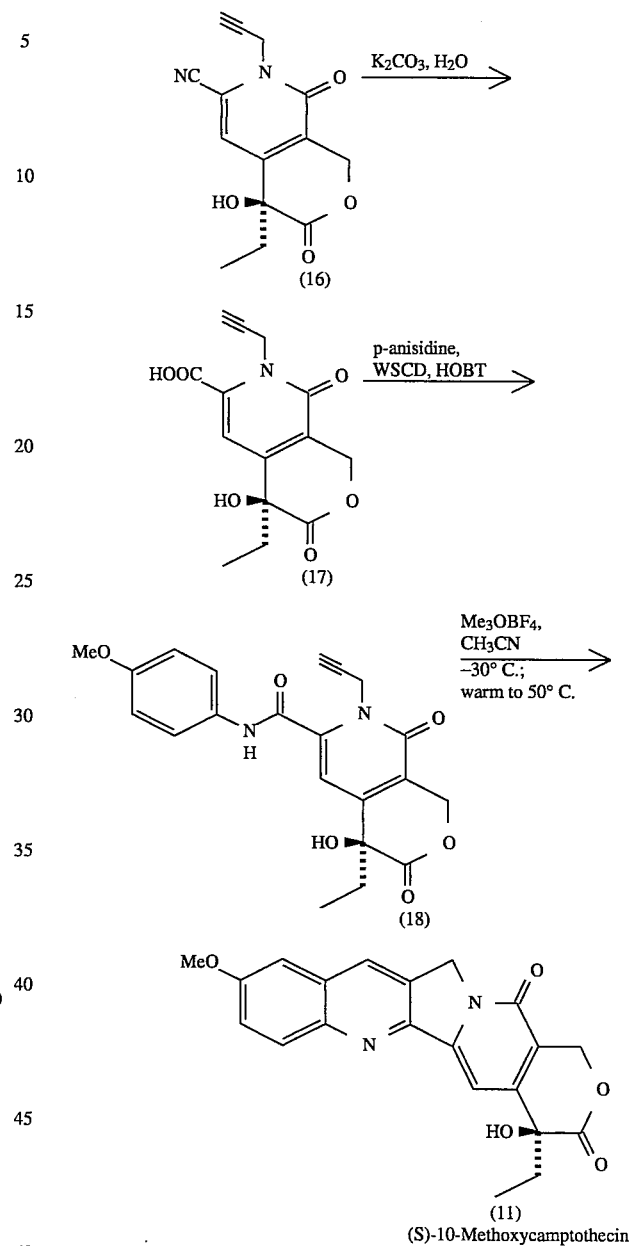

(11)
(S)-10-Methoxycamptothecin

A preferred process of the present invention, which provides for the total synthesis of (S)-10-methoxycamptothecin, is further described in the Example below.

In the following synthetic Example, temperature is in degrees Centigrade (° C). Unless otherwise indicated, all of the starting materials were obtained from commercial sources and used as received. It is believed that one skilled in the art can, using the preceding description, utilize the present invention to its fullest extent. This Example is given merely to illustrate the present invention, and should not be construed as limiting the scope thereof in any way. Reference is made to the claims for what is reserved to the inventor hereunder.

EXAMPLE

The following Example describes a preferred process of the present invention for the total synthesis of (S)-10-methoxycamptothecin, which process is outlined in Schemes 1-4.

Step 1

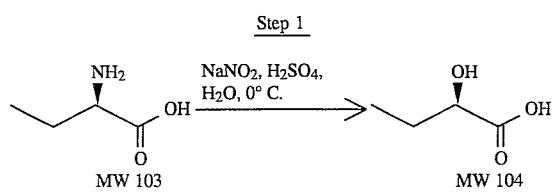

(R)-2-Hydroxybutyric acid is prepared from (R)-2-aminobutyric acid following the procedure of K. Mori et al. described in *Tetrahedron*, 35, 1601, 1979. The reaction product was obtained in approximately 65% yield when carried out on a scale utilizing 50 g of the starting aminobutyric acid. The (R)-2-aminobutyric acid was purchased from the Aldrich Chemical Corp. with a purity of 99%. The chiral purity of the desired (R)-2-hydroxybutyric acid was previously established by Mori as >97%.

Step 2

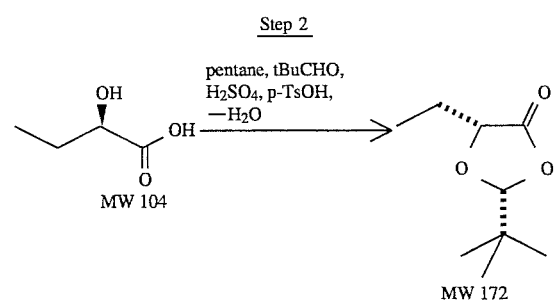

A solution of (R)-2-hydroxybutyric acid (7.2 g, 60 mmol) and 2,2-dimethylpropionaldehyde (11.91 g, 138 mmol, 2.3 eq) in 200 ml of pentane was treated with 250 mg (1.2 mmol, 2 mol %) of p-toluenesulfonic acid and two drops (approximately 50 mg) of concentrated (12 M) aqueous sulfuric acid solution. The solution was heated at reflux for 18 hours with removal of water. The solution was cooled to ambient temperature, washed with 2×100 ml of water and dried over anhydrous magnesium sulfate. The solution was filtered and concentrated under reduced pressure to 11.0 g of a yellow oil. This material was distilled at a pressure of 50 mm Hg to give a main fraction (9.77 g, 82.0% yield) with boiling point of 93°–95° C. The product was examined by $^1$H NMR spectroscopy and determined to be an approximately 28:1 mixture of cis- and trans-dioxolanone ring isomers by comparison of the relative integrations of the methine singlets representing the —CH(tert-butyl) proton for the respective isomers.

The mixture of cis and trans dioxolanones (8.0 g) was dissolved in diethyl ether (about 25 ml) with subsequent cooling in an ice/salt bath to approximately −20° C. The solution was gradually diluted with stirring by the addition of hexane which was precooled to −20° C. Addition was continued until the solution became slightly turbid (approximately 100 ml added). At this point a small mount of additional diethyl ether was added to give a clear solution, and stirring was continued with gradual cooling to −78° C. using dry ice/acetone. A precipitate of fine, white crystals was seen to form upon cooling. The product was collected by rapid decanting of the cold solution, washing with about 25 ml of −78° C. hexane, and filtration at −78° C. using a chilled, jacketed Buchner funnel. The collected product was quickly removed for storage and was observed to melt at approximately −5° C. The presence of the minor, trans isomer of the dioxolanone ring was no longer detectable using $^1$H NMR spectroscopy.

The chirality of the product was determined by $^1$H NMR spectroscopy using a chiral shift reagent Eu(thd)$_3$, (tris(2,2,6,6-tetramethyl-3,5-heptanedionato)europium). A sample of racemic material was prepared from racemic 2-hydroxybutyric acid and recrystallized at low temperature as described above for the chiral product in order to prepare a sample for comparison.

Step 3

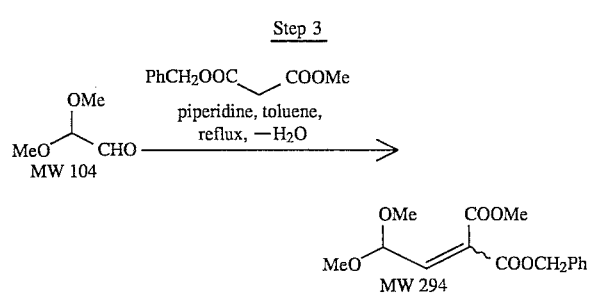

A mixture of 4.16 g (20 mmol) of benzyl methyl malonate, 5.20 g (50 mmol, 2.5 eq) of glyoxal-1,1-dimethyl acetal, 1.7 g (20 mmol, 1.0 eq) of piperidine and 200 ml of toluene was refluxed with azeotropic removal of water using a Dean Stark trap. After 45 minutes the theoretical amount of water had been collected and the mixture was cooled to ambient temperature. The yellow solution was evaporated under reduced pressure and chromatographed on silica gel using methylene chloride as eluent. The fractions containing product were evaporated to give 4.82 g of the desired compound as a colorless oil (82.0% yield).

Step 4

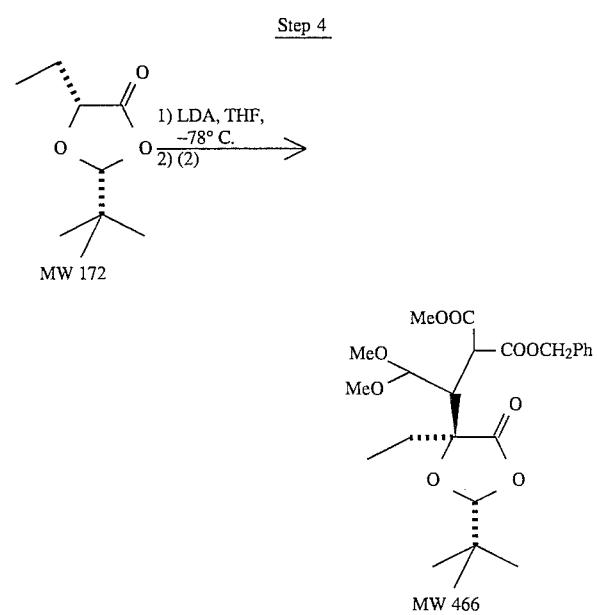

A 2.5 M solution of n-butyllithium in hexane (1.6 ml, 4.0 mmol) was added to a stirred, −78° C. solution of dry diisopropylamine (426 mg, 4.22 mmol) in 40 ml of freshly distilled tetrahydrofuran under an atmosphere of dry nitrogen. The mixture was warmed to 0° C. and stirred for about 30 minutes. The pale yellow solution was then re-cooled to approximately −78° C. with continued stirring.

The dioxolanone (1) prepared as described in Step 1 (765 mg, 4.4 mmol) was dissolved in 5 ml of freshly distilled tetrahydrofuran and cooled to −78° C. in a separate reaction vessel under an atmosphere of dry nitrogen. This solution was then carefully transferred to the freshly prepared solution of lithium diisopropylamide via a double-ended needle over about 10 minutes. The temperature of the lithium diisopropylamide solution was not allowed to rise above about −75° C. during the course of the addition. The reaction solution was stirred for 45 minutes after the addition was complete. During this time a solution of compound (2) was prepared in 5 ml of dry tetrahydrofuran and cooled to −78° C., again under an atmosphere of dry nitrogen. The solution of (2) was added dropwise over about 10 minutes to the stirred enolate solution of (1). After stirring for approximately 3 hours with gradual warming to −20° C. the mixture was quenched by pouring into 30 ml of a half-saturated solution of aqueous ammonium chloride and extracted with 2×50 ml portions of diethyl ether. The combined organic layers were dried over anhydrous sodium sulfate, filtered and evaporated to give 1.70 g of a clear, colorless oil.

The product was chromatographed on 50 g of silica gel using 20% ethyl acetate:hexane as eluent. After evaporation of solvent from the product-containing fractions, a total of 1.08 g (58.1%) of desired product was obtained as a heavy, colorless oil.

Step 5

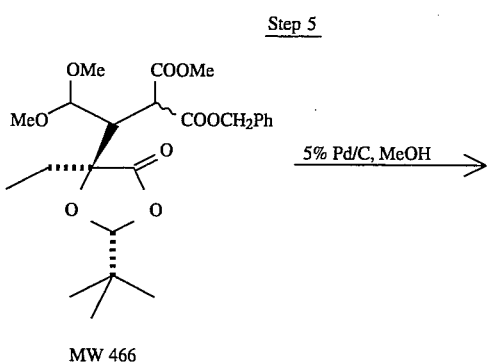

MW 466

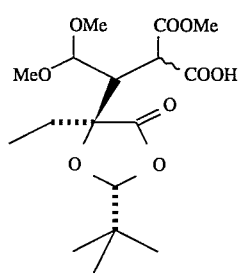

MW 376

A solution of 1.8 g (3.8 mmol) of the benzyl ester in 50 ml of absolute methanol was treated with 250 mg of 5% palladium-on-carbon catalyst and reduced under an atmosphere of hydrogen at 50 psi for 1.75 hours. Hydrogen uptake was essentially complete after about 1 hour. The mixture was vented to nitrogen and purged under an inert atmosphere. The suspension was filtered through a short pad of filter cel with suction to remove the suspended catalyst, and evaporated under vacuum. The colorless oil was dried under a high vacuum (<0.001 mm Hg) to give 1.44 g of a colorless oil (99% yield).

Step 6

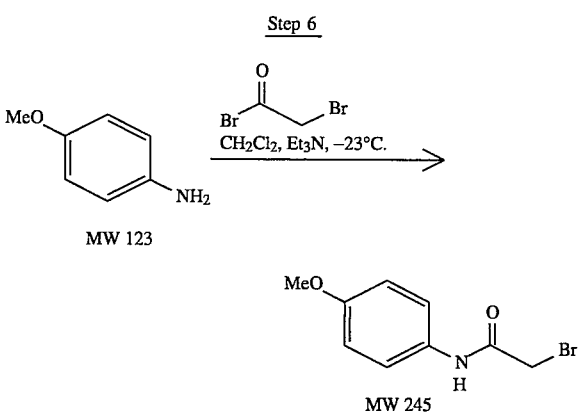

A solution of freshly distilled bromoacetyl bromide (20.22 g, 100 mmol) in 200 ml of methylene chloride was cooled with stirring to −23° C. To this was added a slight excess (11.1 g, 110 mmol) of triethylamine. A solution of p-anisidine (12.3 g, 100 mmol) in 100 ml of methylene chloride was slowly added to the mixture with rapid stirring. A heavy, white precipitate formed upon the addition of the p-anisidine solution. The addition was exothermic and was carried out so that the internal temperature of the solution did not exceed −10° C. Stirring was continued for 1.5 hours after addition was complete. The mixture was diluted with water (200 ml) and subsequently washed with an additional 200 ml of water and 200 ml of 3% aqueous, hydrochloric acid solution. The methylene chloride layer was dried over anhydrous sodium sulfate, evaporated to a yellow-green solid, and triturated with 150 ml of tert-butyl methyl ether to give a white, crystalline powder after filtration. After drying under reduced pressure, 22.5 g (92.3%) of the desired product was obtained.

Step 7

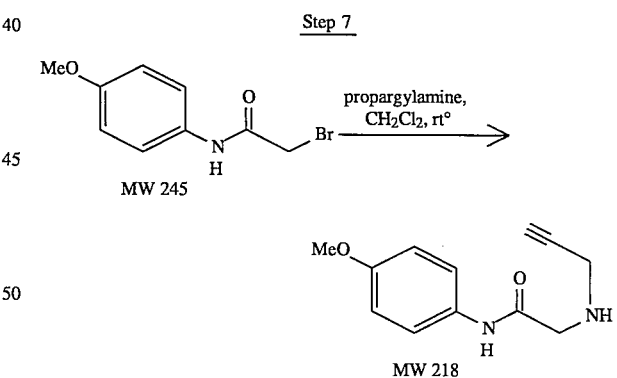

A solution of 11.0 g (200 mmol) of propargylamine in 150 ml of methylene chloride was stirred at ambient temperature. To this was added 12.2 g (50 mmol) of the solid bromide in a single portion. Stirring was continued for a total of about 18 hours, at which time the reaction was complete as judged by analytical thin layer chromatography. The solution was washed with water (100 and 50 ml portions) and dried over anhydrous sodium sulfate. The solution was filtered and evaporated under reduced pressure to yield an orange oil which crystallized under high vacuum to yield 10.77 g of crude product as orange crystals. The product was chromatographed by filtration through 70 g of silica gel using 5% methanol:methylene chloride as eluent. After evaporation of solvent from the product-containing fractions the desired compound was isolated by evaporation of solvent to yield 10.0 g of a pale-orange, crystalline solid (91.7%).

Step 8

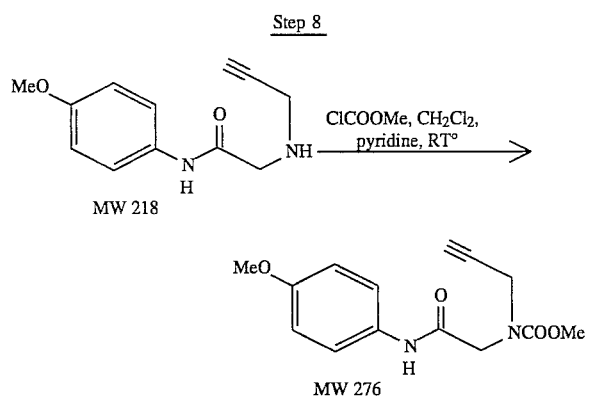

A stirred solution of the secondary propargylamine (2.18 g, 10 mmol) and pyridine (790 mg, mmol) in methylene chloride (25 ml) was treated by the dropwise addition of 950 mg (10 mmol, 1.0 eq) of methyl chloroformate at ambient temperature. The addition was mildly exothermic. The mixture was stirred for a total of about 2 hours, at which time analytical thin layer chromatography indicated that the reaction was complete. The reaction was worked up by the addition of water (25 ml) and additional methylene chloride (25 ml). The organic layer was washed with additional water (2×25 ml) and dried over anhydrous sodium sulfate. After filtration and evaporation, the resulting oil was chromatographed on silica gel (60 g) using 3% methanol:methylene chloride as eluent. The suitable fractions were combined and evaporated to give 1.75 g (63.4% yield) of the desired product as a white solid.

Step 9

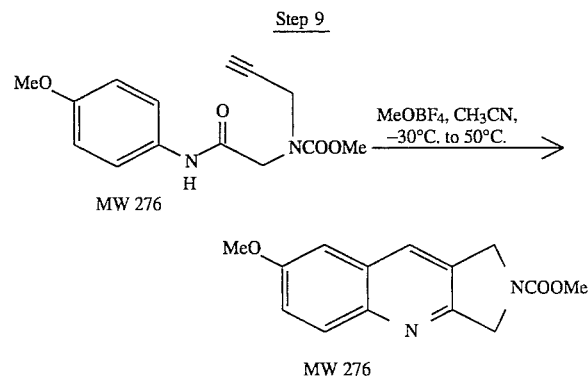

A 100 mg (0.36 mmol) sample of the N-propargyl urethane in solution with 3.0 ml of dry acetonitrile was stirred under an atmosphere of nitrogen at −30° C. To this was added dropwise a solution of 160 mg (1.08 mmol, 3.0 eq) of trimethyloxonium fluoroborate in 3.0 ml of dry acetonitrile. The addition was carded out over about 5–10 minutes so as to maintain the internal temperature of the solution at −30° C. After stirring for one hour at −30° C. and one hour at ambient temperature, the mixture was heated to 50° C. and maintained at this temperature for 24 hours. At this point the solution was cooled to ambient temperature and the solvent was removed under reduced pressure. The residual oil was partitioned between 25 ml each of methylene chloride and water, and the aqueous phase was extracted with 3 additional 25 ml portions of methylene chloride. The combined organic extracts were washed with 50 ml of water, dried over anhydrous sodium sulfate, and evaporated to a brown solid. The solid was recrystallized from methanol to give 155 mg of product (60% yield) which was collected in two crops.

Step 10

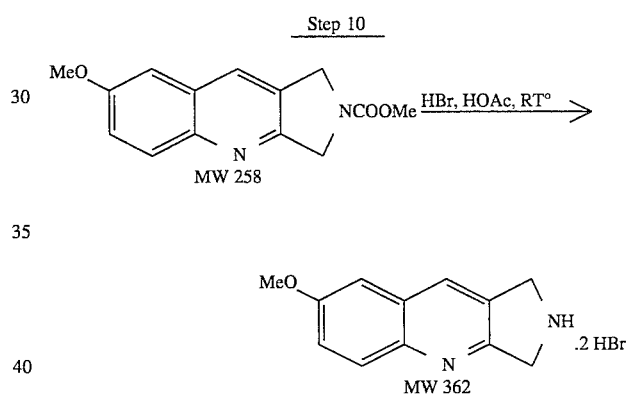

A solution of 1.00 g (3.9 mmol) of the carbamate in 20 ml of acetic acid saturated with hydrobromic acid was refluxed for three hours. During this time an insoluble, white precipitate formed in the solution. The mixture was allowed to stand overnight at ambient temperature to complete the precipitation. The product was isolated by filtration to give 1.45 g (100%) of product after drying under vacuum at 40° C. for 24 hours to a constant weight.

Step 11

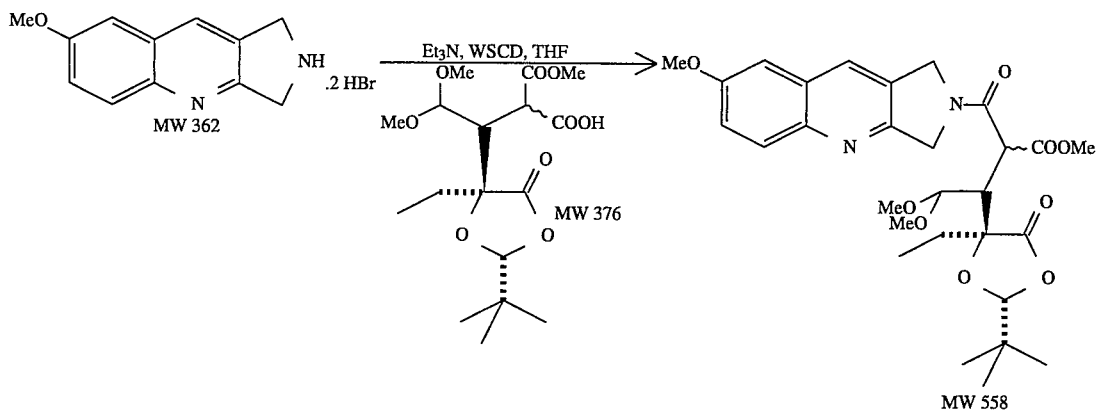

A solution of 863 mg (2.4 mmol) of tricyclic amine dihydrobromide in 30 ml of dry tetrahydrofuran was stirred with 485 mg (4.8 mmol, 2.0 eq) of triethylamine and 507 mg (2.6 mmol, 1.1 eq) of 1-(3-dimethylaminopropyl)-3-ethyl-carbodiimide at ambient temperature under a nitrogen atmosphere. The progress of the reaction was monitored by HPLC using a $C_{18}$ μBondapak column (50% acetonitrile-:water containing 0.1 M sodium perchlorate adjusted to a pH of 2.5 by addition of perchloric acid; detection by UV at a wavelength of 218 nm, flow rate 2.0 ml/min; r.t. of starting amine 1.33 min., r.t. of product 9.88 min.). After 24 hours the starting material had been essentially consumed and the relative peak-area-ratio response for the major product was 93.5%. The reaction was worked up by evaporating the solvent under reduced pressure to a brown oil. The residual material was partitioned between 50 ml each of methylene chloride and water. The aqueous layer was extracted with an additional 50 ml of methylene chloride and the combined organic extracts were dried over anhydrous sodium sulfate, filtered and evaporated to yield 1.5 g of a brown, glassy foam. This residue was chromatographed through silica gel (60 g) using 10% methanol:methylene chloride as eluent. The suitable fractions were combined and evaporated to give 1.0 g of product (74.7% yield) as a yellow oil.

Step 12

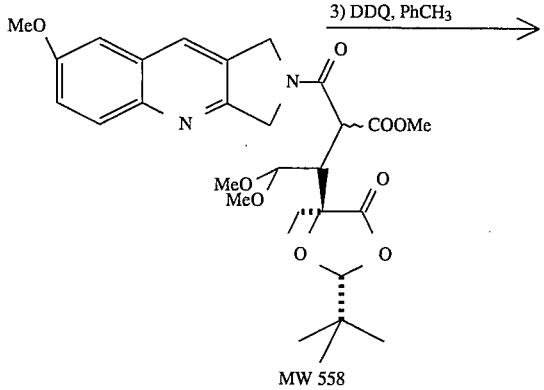

-continued
Step 12

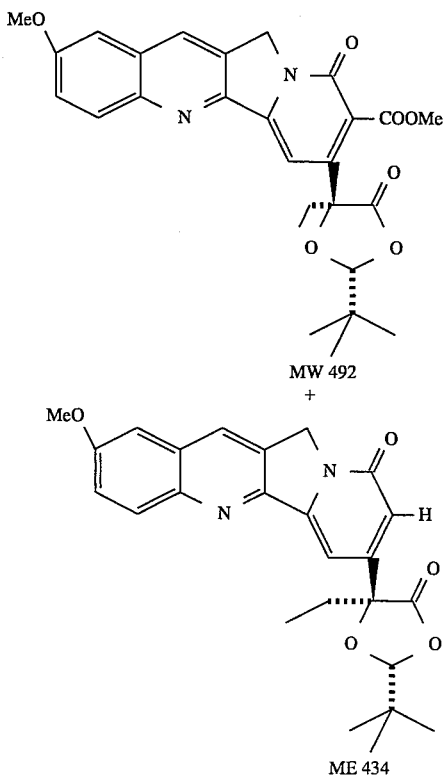

A 500 mg sample of the starting acetal (0.89 mmol) was stirred in a solution of 50 ml of methylene chloride at –78° C. This was treated with 0.8 ml (923 mg, 6.5 mmol, 7.3 eq) of boron trifluoride etherate added in a single portion. The solution was stirred for 20 minutes with continued cooling, then stirred with the cooling bath removed for an additional 20 minutes. The solution was diluted with 25 ml of water, then stirred vigorously for an additional 30 minutes. The pH of the solution was then adjusted to approximately 6.0 by the addition of solid sodium bicarbonate. Stirring was stopped, and the layers of the reaction were separated. The organic layer was dried over anhydrous sodium sulfate, filtered and evaporated to yield 500 mg (450 mg theoretical yield) of a light-colored foam. NMR spectroscopy confirmed that the dimethyl acetal of the starting material had been hydrolyzed to produce the corresponding aldehyde.

The crude aldehyde was dissolved in 35 ml of toluene containing two drops (about 40 mg) of trifluoroacetic acid. The mixture was refluxed for 18 hours, washed with 25 ml of a saturated solution of aqueous sodium bicarbonate and evaporated to give 500 mg of a dark oil. About 460 mg of this crude product was then carded on by dissolution in 45 ml of toluene. The toluene solution was stirred under an atmosphere of nitrogen at ambient temperature, and 460 mg (1.98 mmol, 2.2 theoretical mol eq) of 2,3-dichloro-5,6-dicyanobenzoquinone (DDQ) was added. After stirring for 18 hours the reaction was evaporated to a dark oil, and chromatographed on 100 g of silica gel using 10% methanol:methylene chloride as eluent. Approximately 300 mg of a dark oil was obtained. A portion (approximately one-half) of this crude product was further purified by an additional chromatography on silica gel (30 g). After elution with ethyl acetate to remove non-polar impurities, the product was eluted with 5% methanol:ethyl acetate to yield 35 mg of product. An additional chromatography of this sample was carried out to yield 18 mg of pure product as determined by analytical TLC/HPLC. In addition to the isolation of (10a) from this chromatography, a second compound (9 mg, subsequently identified as compound (10b)) was also isolated as a byproduct.

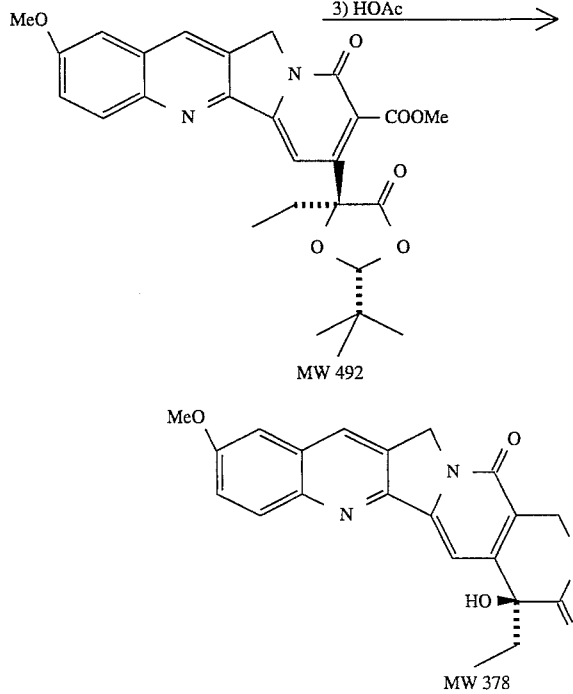

An 11 mg (0.022 mmol) sample of chromatographed ester was dissolved in 1 ml of methylene chloride and stirred under an atmosphere of nitrogen at ambient temperature. The solution was treated with dropwise addition of 0.1 ml (0.11 mmol, 5.0 eq) of diisobutylaluminum hydride added as a 1 M solution in hexane. After stirring for 1 hour, the mixture was partitioned between water (2 ml) and methylene chloride (8 ml). The organic layer was dried over anhydrous sodium sulfate, filtered and evaporated to a heavy oil. Proton NMR spectroscopy indicated that the reduction of the methyl ester to the corresponding alcohol was not complete. A sample of appoximately 8 mg of the residue was then re-dissolved in 2 ml of methylene chloride and cooled to $-10°$ C. This was treated with an additional 0.1 ml (0.11 mmol) of diisobutylaluminum hydride and stirred with slow warming to ambient temperature over about 3 hours. The mixture was evaporated to a heavy oil and dissolved in 3 ml of absolute methanol. A solution of 2 N aqueous sodium hydroxide (1 ml) was added and the mixture was stirred for about 14 hours at ambient temperature. The solution was neutralized by the addition of 500 mg of glacial acetic acid and evaporated to dryness under reduced pressure. The residue was dissolved in 1 ml of 1:1 methylene chloride:methanol and purified by preparative thin layer chromatography using a silica gel matrix. After elution twice with 10% methanol:methylene chloride containing 1% glacial acetic acid the product was isolated as 4.6 mg of a pale-yellow solid (54.5% yield).

The identity and purity of the product was confirmed by comparison of its proton nuclear mass resonance spectrum ($^1$H NMR) mass spectrum including high-resolution exact mass determination (MS) and chromatographic behavior utilizing high pressure liquid chromatography (HPLC) versus an authentic sample of the desired material from natural plant sources. The chirality of the product was determined by HPLC chromatography utilizing a commercially available column packed with a chiral support medium.

$^1$H NMR (DMSO; resonances quoted in ppm downfield from tetramethylsilane): δ0.88 (t, 3H; J=7.2 Hz), 1.88 (m, 2H), 3.32 (br s, due to the presence of HOD), 3.93 (s, 3H), 5.25 (s, 2H), 5.50 (s, 2H), 6.51 (s, 1H), 7.23 (s, 1H), 7.49 (d, 1H; J=7.5 Hz), 7.52 (s, 1H), 8.06 (d, 1H; J=7.5 Hz), 8.54 (s, 1H)

Mass Spectrum (DCI/NH$_3$ ionization): m/z 379 (M+H)$^+$; 335 (M–CO$_2$+H)$^+$ Exact Mass: calculated: 378.12158 found: 378.12159

HPLC conditions

Column:
Two concatenated Techocel OA-3100 columns (total dimensions 50 cm×4.0 mm)
Mobile Phase:
95:5 n-Butyl chloride:Methanol
Temperature:
Ambient
Detector:
UV at a wavelength of 370 nm
Flow Rate:
1.0 ml/minute
Injection Volume:
10 μl
Sample Run: 75 minutes
Sample Prep'n.: Sample is first dissolved in a minimum of N,N-dimethylformamide, followed by diluting to an approximate concentration of 0.1 mg/ml in the mobile phase.

Results of HPLC Analysis

Ret. Time:
41.61 minutes for (R) 10-methoxycamptothecin
45.11 minutes for (S) 10-methoxycamptothecin
Response:
99.1% total peak-area-ratio response for the major compound, (S) 10-methoxycamptothecin
0.55% total peak-area-ratio response for the opposite enantiomer, (R) 10-methoxycamptothecin Step 14

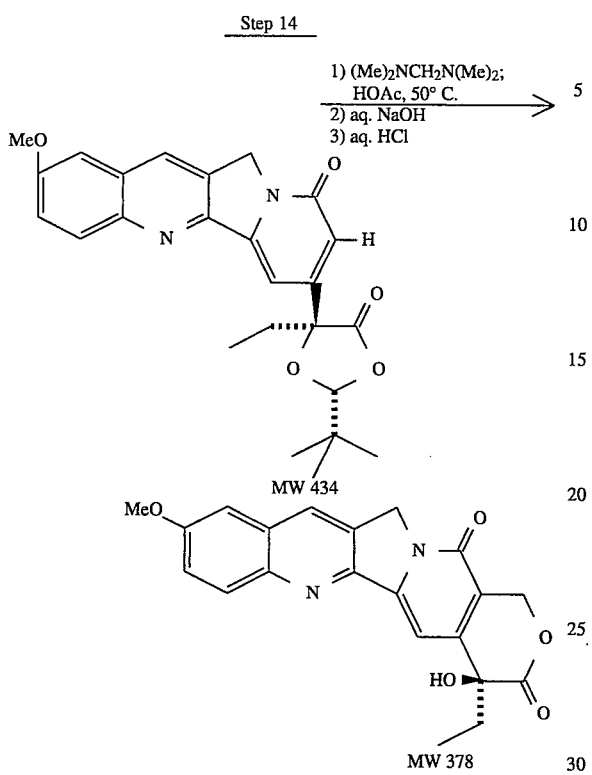

A 16 mg sample (0.037 mmol) of solid, crystalline starting material was stirred with 3 ml of glacial acetic acid at 20° C. to give a clear, pale-yellow solution. To this was added 15 mg (0.15 mmol, 4.0 eq) of 1,1,3,3,-tetramethyl-diaminomethane in a single portion. After stirring for 1.5 hours at ambient temperature, the reaction mixture was heated to 50° C. After stirring for 12 hours, analytical TLC confirmed that no starting material remained in solution. The solution was then concentrated under vacuum at ambient temperature to an oil. The oil was then stirred for 2 hours at ambient temperature with 3 ml of a 2 N aqueous, sodium hydroxide solution. The aqueous solution was carefully acidified to a pH of approximately 3.5–4.0 by the dropwise addition of 5% aqueous, hydrochloric acid solution. A solid was seen to precipitate from the aqueous solution. The aqueous suspension was diluted to a volume of 15 ml and extracted with 3×35 ml portions of 20% methanol:methylene chloride. The organic layers were then combined and evaporated to dryness under reduced pressure. The residual solid was triturated with 5 ml of hot methanol and the product was isolated by filtration. The identity of the product (9.0 mg, 65% yield) was confirmed in the same manner as for the immediately preceding reaction.

What we claim:

1. A process for the asymmetric synthesis of camptothecin analogues comprising:

a) forming a chiral cis dioxolanone having a diester function, of the absolute configuration desired in the camptothecin analogue;

b) converting said cis dioxolanone to form a compound of Formula (I)

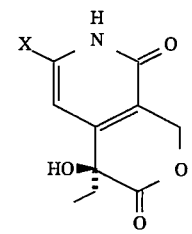

wherein X is selected from a group consisting of a good leaving group, a cyano group, a carboxylic acid, and an N-aryl carboxylic amide derivative of Formula (A);

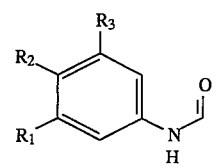

c) converting said compound of Formula (I) into a compound of Formula (II)

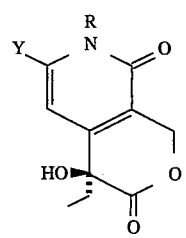

wherein:

R is propargyl or substituted propargyl of Formula (B)

and

Y is selected from a group consisting of a good leaving group, a cyano group, carboxylic acid, and N-aryl carboxylic amide derivative of Formula (A); and d) converting said compound of Formula (II) into a camptothecin analogue.

2. A process according to claim 1 wherein step a) further comprises the step of Michael addition of an enolate of a dioxolanone to diethyl glutonate to form said cis dioxolanone having a diester function.

3. A process according to claim 1 wherein step b) further comprises the following steps:

1) hydrolysis of said diester function of said cis dioxolanone followed by ring closure to form a corresponding glutarimide; and 2) treatment of said glutarimide with an excess of a thionyl halide in dimethylformamide; followed by workup in aqueous base to form a compound of Formula (I) wherein X is bromide or iodide.

4. A process according to claim 3 wherein said thionyl halide is thionyl bromide and said compound of Formula (I) is the compound wherein X is bromide.

5. A process according to claim 1 wherein step b) further comprises the steps of:

1) hydrolysis of said diester function of said cis dioxolanone followed by ring closure to form a corresponding glutarimide; and 2) treatment of said glutarimide with an excess of a sulfonylating agent in dimethylformamide to give a compound of Formula (I) wherein X is a sulfonate.

6. A process according to claim 5 wherein said compound of Formula (I) is a compound wherein X is selected from the group consisting of p-fluorobenzenesulfonate, trifluoromethanesulfonate and fluorosulfonate.

7. A process according to claim 6 wherein said compound of Formula (I) is the compound wherein X is trifluoromethanesulfonate.

8. A process according to claim 1 wherein said step c) further comprises the steps of:

1) formation of a compound of Formula (I) wherein X is cyano;
2) alkylation of the pyridone ring nitrogen of said compound in step 1 ) with propargyl bromide followed by hydrolysis to form a compound of Formula (II) wherein R is propargyl and Y is a carboxylic acid; and
3) coupling said carboxylic acid function of said compound of Formula (II) in step 2) with p-aniside to from a compound of Formula (II) wherein Y is an N-aryl carboxylic amide derivative of Formula (A).

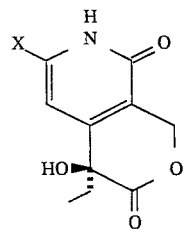
(I)

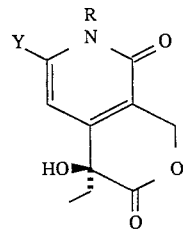
(I)

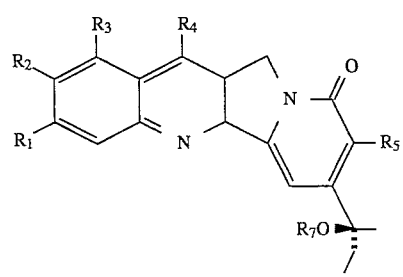
(III)

* * * * *